United States Patent [19]

Agus et al.

[11] Patent Number: 5,100,647
[45] Date of Patent: Mar. 31, 1992

[54] METHOD AND FORMULATIONS FOR THE THERAPY OF CYSIC FIBROSIS, BARTTER'S SYNDROME AND SECRETORY DIARRHEAS, AND FOR DIURETIC TREATMENT

[75] Inventors: Zalman S. Agus, Cherry Hill, N.J.; Ellie Kelepouris, Merion; Martin Morad, Philadelphia, both of Pa.

[73] Assignee: The Trustees of the University of Pennsylvania, Philadelphia, Pa.

[21] Appl. No.: 591,821

[22] Filed: Oct. 2, 1990

[51] Int. Cl.$^5$ ............... A61K 9/12; A61K 31/435
[52] U.S. Cl. .................................. 424/45; 424/46; 514/286; 514/837; 514/851; 514/867; 514/869
[58] Field of Search ............... 514/837, 851, 867, 869, 514/286; 424/45, 46, 44; 546/71

[56] References Cited

U.S. PATENT DOCUMENTS

| | | | |
|---|---|---|---|
| 4,415,577 | 11/1983 | Hachmeister et al. | 514/286 |
| 4,501,729 | 2/1985 | Boucher et al. | 424/45 |
| 4,866,072 | 9/1989 | Edwards et al. | 514/291 |

OTHER PUBLICATIONS

Pharmacognosy; 7th Ed., 1976, Lea & Febiger, pp. 287–288.
Levitan, Irwin B., *Perspective*, Jun. 23, 1989, p. 1423.
Knowles et al., *New England Journal of Medicine*, vol. 322, No. 17, pp. 1189–1194.
Jetten et al., *Science*, vol. 244, Jun. 23, 1989, pp. 1472–1475.
Boucher et al., *J. Clin. Invest.*, vol. 84, Nov. 1989, pp. 1424–1431.
Berschneider et al., *Faseb J.*, 1988 Jul. 2(10) Abstract.
Paolisso et al., *Biochem. Pharmacol.*, 1985 Jul. 1;34(13) Abstract.
Paolisso et al., *Horm. Metabol.*, 1988, pp. 658–659.
Dukes et al., *The Journal of Pharmacology and Experimental Therapeutics*, vol. 254, No. 2, May 10, 1990.
Dubinsky, *Hospital Practice*, Jan. 15, 1989, pp. 69–82.
Hwang et al., *Reports*, Jun. 16, 1989, pp. 1351–1356.

*Primary Examiner*—Thurman K. Page
*Assistant Examiner*—D. Colucci
*Attorney, Agent, or Firm*—Oblon, Spivak, McClelland, Maier & Neustadt

[57] ABSTRACT

Methods for the therapy of cystic fibrosis, Bartter's syndrome, and secretory diarrheas, and for diuretic treatment, by administering to a patient dodecahydro-7,14-methano-2H,6H-di-pyrido[1,2-a:1',2'-e][1,5]diazocine or a pharmaceutically acceptable derivative thereof are disclosed. The formulations include an aerosol formulation comprising the active ingredient in association with an aerosol propellant.

19 Claims, No Drawings

METHOD AND FORMULATIONS FOR THE THERAPY OF CYSIC FIBROSIS, BARTTER'S SYNDROME AND SECRETORY DIARRHEAS, AND FOR DIURETIC TREATMENT

BACKGROUND OF THE INVENTION

1. Field of the Invention

The present invention relates to methods and formulations for the therapy of cystic fibrosis, Bartter's syndrome and secretory diarrheas such as cholera, and for diuretic treatment.

2. Discussion of the Background

Cystic fibrosis: This is a congenital disease for which an accurate diagnosis has long been available. Historically, a midwife would lick the forehead of a newborn. If the sweat tasted abnormally salty, the infant was destined to die of pulmonary congestion and its side effects. Today, cystic fibrosis remains the most common lethal congenital disease among caucasians where it has a prevalence of about of about 1 in 2,000 live births.

Cystic fibrosis is a disease of secretory epithelia, tissues that mediate the transport of water, salt, and other solutes between the blood and the outside world. Epithelial cells exhibit anatomical and functional polarity. The basolateral membrane, which faces the blood, and the apical membrane, which faces the lumen (the outside world) mediate different transport events. Together they give rise to net chloride transport across the epithelium from blood to lumen.

Sodium and water accompany the transport of chloride, resulting in secretion of a solution of sodium chloride into the lumen. The secretion requires activation of the secretory pathways by hormones and neurotransmitters, which utilize the intracellular second messengers adenosine 3',5'-monophosphate (cyclic AMP) or calcium.

Although the survival of cystic fibrosis has improved in recent years, the median survival is still only about 25 to 30 years despite intensive supportive and prophylactic treatment. There is thus a clear need for new therapeutic approaches to this uniformly fatal disease in which, all patients suffering from the disease develop chronic progressive disease of the respiratory system. The most common cause of death is pulmonary disease. Also, in the majority of cystic fibrosis patients, pancreatic dysfunction occurs, with hepatobiliary and genitourinary diseases being also frequent.

The clinical manifestations of the disease appear to be consequences of the secretory defect with diminished secretions producing obstruction of airways and pancreatic output. Current therapeutic approaches are designed to improve air flow indirectly by bronchodilatation, reduction of inflammation with glucocorticoids and control of superimposed infections with antibiotics. Most recently, direct attempts to improve quality of secretions have been made utilizing aerosolized amiloride (U.S. Pat. No. 4,501,729) or 9-ethyl-6,9-dihydro-4,6-dioxo-10-propyl-4H-pyrano(3,2-g)quinoline-2,8-dicarboxylic acid or a pharmaceutically acceptable derivative thereof (U.S. Pat. No. 4,866,072).

Amiloride aerosol appears to slow the decline in pulmonary function associated with cystic fibrosis. These beneficial effects are attributed to increased clearance of secretions, presumably due to reduced sodium absorption. This treatment however does not address the primary abnormality of the disease.

Recent studies have provided new information concerning the abnormalities in cellular transport which underlie the secretory defect in cystic fibrosis. There is now direct evidence indicating that the chloride channel in cystic fibrosis airway epithelia does not activate in response to cAMP as it does in normal airway cells. At present, although direct exogenous activators of the chloride conductance have not been identified or characterized, the development of such compounds should prove to be extremely beneficial, either alone or in combination with alteration of sodium transport.

Bartter's syndrome: In 1962 Bartter described a syndrome consisting of hypokalemia due to renal potassium wasting, elevated plasma renin activity, and aldosterone secretion, normotension, hyporesponsiveness of blood pressure to infused angiotensin II and hyperplasia of the granular cells of the juxtaglomerular apparatus. Weakness, or periodic paralysis, and polyuria occurred because of chronic potassium depletion. Hyperplasia of renal medullary interstitial cells, which produce prostaglandins (PG) E and F, has been described in some patients, along with very elevated $PGE_2$ production. Inheritance is autosomal recessive. Manifestations commonly begin in childhood.

While the pathogenetic sequence of this disease has not been proved with certainty, depressed reabsorption of certain chloride in the proximal tubule or thick ascending limb of the loop of Henle is thought to be the basic underlying defect in this syndrome. The exact basis for the tubular reabsorptive defect is uncertain, but it may be part of a widespread inherited disorder.

Excessive sodium chloride losses in the urine causes depletion of extracellular fluid volume, which in turn stimulates hyperplasia of the granular cells of the juxtaglomerular apparatus and increases renin production. The resulting increase in angiotensin II production stimulates aldosterone secretion. Renal tubular defect permits continued delivery of sodium to the sodium-potassium exchange sites in the distal nephron, which are stimulated by a supernormal concentration of serum aldosterone, and renal wasting of potassium ensues. Blood pressure remains normal because the pressure effects of angiotensin II are offset by depletion of extracellular volume. Infusion of angiotensin II produces less than the usual rise in arterial pressure because angiotensin II levels are already elevated.

With patients suffering from Bartter's syndrome, the dietary intake of sodium chloride and potassium is liberal. Often potassium supplements are required despite a high dietary intake. Pharmacological blockage of aldosterone effects on distal tubules with spironolactone can prevent potassium wasting, though sodium intake must be increased. Inhibition of prostaglandin synthesis with indomethacin has met with varying success. Beta adrenergic blockade has also been used, with some success, to lower renin production. But there is a clear need for new therapies directed at stimulating sodium chloride reabsorption in the kidney.

Secretory diarrheas: Cholera is a secretory diarrhea caused by infection with vibrio cholera organisms. The organisms produce an exotoxin which causes the cells lining the intestine to secrete sodium, chloride and water. The massive secretion causes loss of extracellular fluid volume leading to lowering of blood pressure, shock and death if not appropriately treated. Untreated the disease lasts for 2 to 7 days. Current therapeutic regimens include tetracycline to treat the organism and replacement of fluids parenterally and orally. The availability of an orally effective compound which would reduce secretion would have major therapeutic benefits in this disease.

Diuresis: Diuretics are drugs which increase the urinary excretion of sodium and chloride by interfering with normal transport processes at various sites along the nephron of the kidney. They are used in the treatment of disease with increased sodium, chloride and fluid retention such as congestive heart failure, hypertension, cirrhosis and nephrotic syndrome.

Potent diuretics usually work in the ascending limb of the loop of Henle where 20 to 30% of the filtered load is reabsorbed. These drugs include ethacrynic acid, furosemide and bumetanide. A major side effect of these drugs is loss of potassium in the urine with consequent lowering of potassium concentration in the blood (hypokalemia). This is due to increased potassium secretion into the urine by cells lining portions of the nephron distal to the loop of Henle in response to increased delivery of sodium from the loop of Henle. A potent diuretic which inhibits chloride (and sodium transport) in the loop of Henle and also blocks potassium secretion in more distal portions would be a significant improvement over currently available drugs.

SUMMARY OF THE INVENTION

Accordingly, it is an object of this invention to provide a therapy of cystic fibrosis, Bartter's syndrome and secretory diarrheas. It is also an object of this invention to provide a new diuretic.

It is another object of this invention to provide formulations useful in the therapy of cystic fibrosis, Bartter's syndrome, diuresis and secretory diarrheas.

The above objects, and other objects which will become apparent from the description of the invention given hereinbelow, have now been discovered by the inventor to be satisfied by administering to a patient suffering from either cystic fibrosis, Bartter's syndrome or a secretory diarrhea, or in need of diuretic treatment, an amount of dodecahydro-7,14-methano-2H,6H-dipyrido[1,2-a:1',2'-e][1,5]diazocine (Sparteine), or a pharmaceutically acceptable derivative thereof, effective to obtain therapy of said cystic fibrosis, Bartter's syndrome, or secretory diarrhea, or use as a diuretic. The Sparteine or pharmaceutically acceptable derivative thereof may be administered to the patient by any known method of administering a pharmaceutical compound, including orally, parenterally, by inhalation spray, or rectally. Of these methods, administration directly to the airway, e.g., as a pressurized aerosol or as a nebulized solution, is preferred for patients with cystic fibrosis. Oral administration with subsequent absorption is preferred for Bartter's Syndrome and use as a diuretic. Oral administration of a non-absorbable preparation is preferred for patients with secretory diarrhea such as cholera.

DETAILED DESCRIPTION OF THE PREFERRED EMBODIMENTS

Sparteine (dodecahydro-7,14-methano-2H,6H-dipyrido[1,2-a:1',2'-e][1,5]diazocine; 1-Sparteine; lupinidine) is a known compound of the formula:

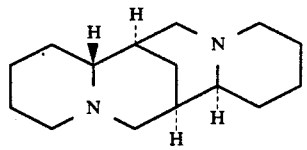

described, for example, in "The Merck Index", 9th ed., published by Merck & Co., Inc., Rahway, N.J. (U.S.A.), pg. 8513 (1976).

Sparteine base which exists as an oil, has two tertiary amino nitrogens and readily forms crystalline salts. The commercially available form is the monosulfate, pentahydrate salt which is water soluble and stable. Stereoisomers exist, 1-sparteine being the naturally occurring form.

Sparteine sulfate, an alkaloid purified from lupin beans, has been utilized intramuscularly as an oytocic drug since 1939 (Goodman L. S. and Gilman A: 1971. In: The Pharmacological Basis of Therapeutics (Eds. Goodman L. S. and Gilman A.) p.905, McMillan Pub. Co.). It has also been shown to enhance insulin secretion in healthy human beings and to increase glucagon secretion in insulin-dependent diabetics (Sgambato S., Passariello N., Paolisso G., Biseti V. and Tesauro P.: 1986. Effect of sparteine sulphate on insulin secretion in normal man. Horm Metab Res. 18:686–698; Sgambato S., Paolisso G., Passariello N., Varricchio M., and D'Onofio F.: 1987. Sparteine sulfate effects upon basal and nutrients induced insulin and glucagon secretion in normal man. Eur J. Clin. Pharm. 32:477–480; and Paolisso G., Sgambato S., Passariello N. et al.: 1988. Plasma glucose lowering effect of sparteine sulfate infusion in non-infusion in non-insulin dependent (type 2) diabetic subjects. Eur. J. Clin. Pharm. 34:227-232). In non-diabetic obese individuals, intravenous administration produced a significant increase in insulin secretion and enhanced the response to simultaneously administered arginine (Paolisso G., Sgambato S., Tesauro P., Varrichio M. and D'Onofrio F: 1988. Sparteine sulfate prevalently stimulates B rather than A cell secretion in obese subjects. Horm Metab Res. 20:658-9). Studies have not clearly defined a mechanism of these effects, but there is evidence that Sparteine sulfate decreases the potassium conductance of pancreatic beta cells (Paolisso G., Nenquin M., Schmeer W., Mathot F. et al: 1985. Sparteine increases insulin release by decreasing the K+ permeability of the B-cell membrane. Biochem. Pharmacol. 34:2355–61).

Sparteine has also been shown to act as a potassium channel blocker in olfactory tract axons (Galvans M., Franz P. and Vogel-Wiens C.: 1984. Actions of potassium channel blockers on guinea pig lateral olfactory tract axons. Naunyn Schmeidebergs Arch Pharmacol 325:8–11) and is classified as a Class 1 cardiac antiarrhythmic due to its effects on sodium channels (Honerjager P., Loibl E., Steidl I, Schonsteiner G., and Ulm K:1986. Negative inotropic effects of tetrodotoxin and seven class 1 antiarrhythmic drugs in relation to sodium channel blockade. Naunyn Schmiedeberqs Arch Pharmacol. 332:184–84). These effects require millimolar concentrations of the drug. To date however, no effects of Sparteine or its derivatives on chloride channels have been reported.

Chloride channels exist in several types of epithelial tissues with a function to produce secretions (e.g., airway epithelia) or absorption (portions of the kidney, colonic mucosa) of salt in water. In these tissues, activation of the chloride channels is produced by phosphorylation in response to increases in cell calcium concentration or certain protein kinases (which in turn are deactivated by hormonal agents). Congenital disorders due to the dysfunction of and inability to activate these channels include cystic fibrosis and Bartter's syndrome. Bacterial toxins such as cholera toxin produce irreversible activation of these channels leading to uncontrolled secretion and diarrhea. Prior to the present invention no pharmaceuticals were known to activate these chloride channels or have therapeutic effects in these disorders.

The present invention is based on the inventors' discovery that Sparteine and its pharmaceutically acceptable derivatives are very potent modulators of chloride channels. The inventors have discovered that Sparteine and its pharmaceutically acceptable derivatives are very potent activators of chloride channels at low (nanomolar) doses and potent inhibitors (blockers) of chloride channels at higher (micromolar to millimolar) doses.

As an activator of chloride channels, Sparteine and its pharmaceutically acceptable derivatives may be used in the therapy of cystic fibrosis and Bartter's syndrome. As inhibitors (blockers) of chloride channels, Sparteine and its pharmaceutically acceptable derivatives may be used in the therapy of secretory diarrhea and as a diuretic.

The pharmaceutically acceptable derivatives which can be used in accordance with the invention also include pharmaceutically acceptable salts derived from inorganic or organic acids. Included among such salts are the following: sulfate, adipate, alginate, aspartate, benzoate, benzenesulfonate, busulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxymethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecenoate.

The compositions of the present invention may be administered orally, parenterally, by inhalation spray, or rectally, in dosage unit formulations containing conventional non-toxic pharmaceutically acceptable carriers, adjutants and vehicles as known in this art. The term parenteral as used herein includes subcutaneous injections, intravenous, intramuscular, intrasternal injection or infusion techniques.

A specific advantage of the present invention, in its application to cystic fibrosis, is the delivery of the active agent to the airway epithelia (the cells which exhibit impaired chloride transport in cystic fibrosis) by aerosol. This eliminates the need for systemic therapy and bypasses potential toxicity from other effects (such as alteration of potassium levels).

Thus, for the therapy of cystic fibrosis in accordance with a preferred embodiment of the present invention, Sparteine or a pharmaceutically acceptable derivative thereof, is preferably directly administered to the patient's lungs, either as a pressurized aerosol or as a nebulized solution. Solutions for administration by nebulization are preferably aqueous solutions designed to provide a final concentration of 0.05 to 1.0, preferably to 0.2, nanomolar (nM) Sparteine sulfate at the airway surface. But the concentration used depends, of course, among other factors, on the severity of the disease.

The dosage of administration of the active ingredient for the therapy of cystic fibrosis and Bartter's syndrome in accordance with the present invention of course varies with, among other factors, the particular active ingredient used, the method of administration, and the severity of the disease. In general, an oral dosage of from about 0.1 to 10 milligrams, designed to produce a blood level of 0.05 to 0.2 nM, administered one to eight, preferably two to six, and most preferably two to four times a day, is satisfactory. A preferred total daily dosage for adult patients is from about 1 to 50 milligrams, preferably from 1 to 10 milligrams. For children, especially infants, the daily dosage used can be the lower end of this range, or may even be less than this. In general, the treatments continued for a period of several months or years, possible throughout the Cystic Fibrosis or Bartter's syndrome patient's lifetime.

For use as a diuretic, the oral administration may be 10 to 100 mg per administration to produce blood levels of 1 to 10 micromolar. In use as a diuretic, the Sparteine or pharmaceutically acceptable derivative thereof, is used to treat hypertension and/or congestive heart failure in a patient suffering from such conditions. For the therapy of secretory diarrheas, such as cholera, the dosage of oral administration may be 1 to 10 mg administered in nonabsorbable form designed to produce a tissue concentration of 1 to 10 micromolar.

In accordance to a preferred embodiment of the present invention, Sparteine or a pharmaceutically acceptable derivative thereof, is present as a medicinal aerosol formulation permitting its administration directly to the cystic fibrosis patient's lungs. In particular, this medicinal aerosol formulation may contain a known aerosol propellants, including chlorofluorocarbon aerosol propellants known useful for endopulmonary and/or nasal inhalation administration. Such medicinal aerosol formulations generally contain a mixture of chlorofluorocarbons, for example, trichloromonofluoromethane (propellent 11), dichlorotetrafluoroethane (propellent 114) or dichlorodifluoromethane (propellent 12). The active ingredient is present as a solution in the aerosol formulation.

In addition to the active ingredient and water, the aqueous solutions may contain co-solvents that are miscible with water and suitable surfactants can be used to achieve solutions for parenteral use. The most important solvents in this group are ethanol, polyethylene glycols of the liquid series and propylene glycol. A more comprehensive listing includes acetone, dimethyl acetamide, dimethyl formamide, dimethyl sulfoxide ethanol, glycerin, polyethylene glycol 300, and 400, propylene glycol, sorbitol, polyoxyethylene sorbitan fatty acid esters such as laureate, a palmitate, stearate, and oleate, polyoxyethylated vegetable oil, sorbitan monopalmitate, 2-pyrrolidone; n-methyl-2-pyrrolidine; n-ethyl-1-pyrrolidine and tetrahydrofurfuryl alcohol.

Other additives may be necessary to enhance or maintain chemical stability and physiological suitability. Examples are antioxidants, chelating agents, inert gases, buffers and isotonicifiers.

Examples of antioxidants and typical concentration ranges include acetone sodium bisulfite (0.1–0.8 wt. %), ascorbic acid (0.05–1.0 wt. %), monothioglycerol (0.1–1.0 wt. %), potassium metabi-sulfite (0.01–1.0 wt. %), sodium formaldehyde sulfoxylate (0.03–0.1 wt. %), sodium metabisulfite (0.02–0.25 wt. %), sodium sulfite (0.01–0.1 wt. %), sodium thioglycolate (0.03–0.1 wt. %).

Examples of chelating/complexing agents and typical concentration ranges include edentate sodium (0.005–0.1 wt. %), edentate calcium disodium (0.005–0.01 wt. %), gentisic acid ethanolamide (1.0–2.0 wt. %), niacinamide (1.0–2.5 wt. %), sodium citrate (0.01–2.5 wt. %), citric acid (0.001–1.0 wt. %).

Examples of inert gases are nitrogen and carbon dioxide. Buffers are used primarily to stabilize a solution against the chemical degradation that might occur if the pH changed appreciably. Buffer systems employed normally have as low a buffer capacity as feasible in order to not disturb significantly the body buffer systems when injected. The buffer range and effect of the buffer on activity must be evaluated. Appropriate adjustment is useful to provide the optimum conditions for pH dependent partition into the target malignant tissues or lesion area.

Examples of such buffer systems include the following acids: acetic, adipic, ascorbic, benzoic, citric, glycine, lactic, tartaric, hydrochloric, phosphoric, sulfuric, and carbonic and bicarbonic; and their corresponding salts such as: potassium, sodium, magnesium, calcium and diethanolamine salts.

Osmolality is of great importance and hypotonic solutions usually have their tonicity adjusted by the addition of salts such as sodium chloride, potassium chloride, magnesium chloride and calcium chloride and sugars such as dextrose, lactose, mannitol and sorbitol.

When the solution is to be dispensed from multiple dose containers, antimicrobial agents in bacteriostatic or fungi-static concentrations must be added. Among the compounds and concentrations most frequently employed are phenylmercuric acid (0.002–0.1 wt. %), thimerosal (0.01 wt. %), benzethonium chloride (0.01 wt. %), benzalkonium chloride (0.02 wt. %), phenol or cresol (0.5 wt. %), chlorbutanol (0.5 wt. %), benzyl alcohol (2.0 wt. %), methyl p-hydroxybenzoate (0.18 wt. %), and propyl p-hydroxybenzoate (0.02 wt. %).

After the solution of the active ingredient with its solvents and additives has been compounded, the solution is filtered to remove particulate matter above $2\mu m$ in size and a further step eliminating particulate matter down to $0.2\mu m$ can eliminate microorganisms and accomplish cold sterilization. The solution is filled under aseptic conditions. The final solution can be additionally sterilized in its final container by thermal methods such as autoclaving or non-thermal methods such as ionizing radiation. The process of freeze drying (lyophilization) can be employed to avoid adverse thermal and oxidative decomposition and provide enhanced stability and improved solubility.

In another embodiment, the pharmaceutical compositions containing the active ingredient in accordance with the invention may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents in order to provide a pharmaceutically elegant and palatable preparation.

Tablets containing the active ingredient in admixture with non-toxic pharmaceutically acceptable excipients which are suitable for manufacture of tablets may be used. These excipients may be, for example, inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example polyoxyethylene stearate, or condensation products of ethylene oxide with long chamin aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mono-oleate. The aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compositions of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Having generally described this invention, a further understanding can be obtained by reference to certain specific examples which are provided herein for purposes of illustration only and are not intended to be limiting unless otherwise specified.

EXAMPLES

Using isolated cells from a cultured kidney cell line, we tested the effects of various doses of Sparteine applied to the interior and exterior of the cell on current through the chloride channel as measured with standard patch clamp electrophysiologic techniques. Cells were dialyzed with a solution containing ATP, no cAMP and 10 nM calcium. Under these conditions, control cells exhibited a peak current of approximately 10 $\mu m/cm^2$ when depolarized to +70 mV from a holding potential of $-45$ mV. Addition of cAMP, calcium or phorbol ester to the internal solution significantly increased the current to maximum levels of approximately 40–50 $\mu M/cm^2$ consistent with studies described by others in other epithelial cells containing these types of chloride channels.

With addition of Sparteine in concentrations of 0.1, 50 and 500 $\mu M$, the current ranged between 80–200 $\mu A/cm^2$, significantly greater than any of the known activators and 10–20 X the control value. With increasing dose (above 0.1 $\mu M$), there was an increasingly rapid decline in the activated current. Externally applied Sparteine was equally or more potent with marked augmentation of the chloride current in concentrations of 0.1 to 10 nM. Thus Sparteine is a very potent activator of the chloride channel at low (pico-nanomolar) concentrations and a potent inhibitor at higher (micromolar-millimolar) concentrations.

An aliquot of cells from a cell line, CF/T43, derived from airway epithelia from a patient with cystic fibrosis were used. These cells exhibit the chloride conductive defect characteristic of cystic fibrosis cells and do not respond to increased intracellular levels of cyclic AMP.

Data were obtained using internal and external solutions as described by McCann, Li and Welsh in studies of whole cell $I_{Cl}$ in normal human airway epithelial cells so as to be able to compare our data with theirs. The internal solutions are cesium-based providing a minimal internal calcium concentration (nominally 0–10 nM, with EGTA) and the external solution is sodium-based with symmetrical Cl concentrations of 140 mM. No cyclic nucleotides are included in the solutions and amiloride is added to block the sodium conductance. When dialyzed with control solutions, the cells exhibited a small linear current with an apparent reversal potential which varied from $-30$ to $-50$ mV.

With addition of external 0.1 nM Sparteine, however, there was a marked increase in current amplitude with appearance of an outwardly rectifying current which shifted the reversal potential toward the right. At extreme depolarizations of +50, +60 and +70 mV, there was the appearance of a time-dependent component to the peak current with a rapid activation and inactivation as described by others in normal human airway epithelial cells. Sparteine increased both inward and outward current amplitudes but rectified in the outward direction. The activated current was reversible with washout of the Sparteine. We have reproduced these observations in multiple cells from 3 different preparations (passages 51–53). The induced current observed was clearly outwardly rectifying with a reversal potential of 0 mV, the $E_{Cl}$ in these solutions.

Thus, pM Sparteine induces a chloride current in cystic fibrosis cells, in the absence of cytosolic $Ca^{2+}$ and cyclic nucleotides.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A formulation suitable for administration as an aerosol or by nebulization comprising dodecahydro-7,14-methano-2H,6H-di-pyrido[1,2-a:1',2'-e][1,5]diazocine or a pharmaceutically acceptable derivative thereof solubilized in a solvent and present therein in an amount effective for the therapy of cystic fibrosis, Bartter's syndrome, or secretory diarrhea, or for diuretic therapy.

2. The formulation of claim 1, comprising said dodecahydro-7,14-methano-2H,6H-di-pyrido[1,2-a:1',2'-e][1,5]diazocine or said pharmaceutically acceptable derivative thereof present, in said solvent, in an amount sufficient to provide a concentration of about 0.05 to about 1.0 nanmolar over most of a patient's airway surface.

3. The formulation of claim 2, wherein said amount is from about 0.05 to 0.2 nanomolar.

4. The formulation of claim 1, comprising dodecahydro-7,14-methano-2H,6H-di-pyrido[1,2-a:1',2'-e][1,5]diazocine or a pharmaceutically acceptable salt thereof.

5. A pressurized aerosol in accordance with claim 1.

6. A formulation suitable for administration by nebulization in accordance with claim 1.

7. A method for the therapy of cystic fibrosis, Bartter's syndrome, or secretory diarrhea, or for diuretic therapy, comprising administering to a patient suffering therefrom a quantity of dodecahydro-7,14-methano-2H,6H-di-pyrido[1,2-a:1',2'-e][1,5]diazocine or a pharmaceutically acceptable derivative thereof effective for said therapy.

8. A method for the therapy of cystic fibrosis according to claim 7 comprising administering to said patient suffering therefrom a quantity of dodecahydro-7,14-methano-2H,6H-di-pyrido[1,2-a:1',2'-e][1,5]diazocine or a pharmaceutically acceptable derivative thereof effective for the therapy of cystic fibrosis.

9. The method of claim 8, comprising administering to said patient dodecahydro-7,14-methano-2H,6H-di-pyrido[1,2-a:1', 2'-e][1,5]diazocine or a pharmaceutically acceptable salt thereof.

10. The method of claim 9, comprising administering said dodecahydro-7,14-methano-2H,6H-dipyrido[1,2-a:1', 2'-e][1,5]diazocine or said pharmaceutically acceptable derivative thereof directly to said patient's lungs.

11. The method of claim 10, comprising administering dodecahydro-7,14-methano-2H,6H-di-pyrido[1,2-a:1', 2'-e][1,5]diazocine or a pharmaceutically acceptable salt thereof.

12. A method for the therapy of Bartter's syndrome according to claim 7 comprising administering to a patient suffering therefrom a quantity of dodecahydro-7,14-methano-2H,6H-di-pyrido[1,2-a:1',2'-e][1,5]diazocine or a pharmaceutically acceptable derivative thereof effective for the therapy of Bartter's syndrome.

13. The method of claim 12, comprising administering to said patient dodecahydro-7,14-methano-2H,6H-di-pyrido[1,2-a:1',2'-e][1,5]diazocine or a pharmaceutically acceptable salt thereof.

14. A method for the therapy of secretory diarrhea according to claim 7 comprising administering to a patient suffering therefrom a quantity of dodecahydro-7,14-methano-2H,6H-di-pyrido[1,2-a:1',2'-e][1,5]diazocine or a pharmaceutically acceptable derivative thereof effective for the therapy of secretory diarrhea.

15. The method of claim 14, comprising administering to said patient dodecahydro-7,14-methano-2H,6H-di-pyrido[1,2-a:1',2'-e][1,5]diazocine or a pharmaceutically acceptable salt thereof.

16. The method of claim 14, wherein said secretory diarrhea is cholera.

17. The method of claim 15, wherein said secretory disease is cholera.

18. A method for the diuretic therapy of a patient according to claim 7 comprising administering to a patient in need thereof a quantity of dodecahydro-7,14-methano-2H,6H-di-pyrido[1,2-a:1,40 ,2'-e][1,5]diazocine or a pharmaceutically acceptable derivative thereof effective for said diuretic therapy.

19. The method of claim 18, comprising administering to said patient dodecahydro-7,14-methano-2H,6H-di-pyrido[1,2-a:1',2'-e][1,5]diazocine or a pharmaceutically acceptable salt thereof.

* * * * *

UNITED STATES PATENT AND TRADEMARK OFFICE
CERTIFICATE OF CORRECTION

PATENT NO. : 5,100,647
DATED : March 31, 1992
INVENTOR(S) : Zalman S. Agus et al.

It is certified that error appears in the above-identified patent and that said Letters Patent is hereby corrected as shown below:

On the title page: Item [54]
Column 1, line 2
The title is incorrect, should be, --METHOD AND FORMULATIONS FOR THE THERAPY OF CYSTIC FIBROSIS, BARTTER'S SYNDROME AND SECRETORY DIARRHEAS, AND FOR DIURETIC TREATMENT--.

Signed and Sealed this

Twenty-second Day of June, 1993

Attest:

MICHAEL K. KIRK

Attesting Officer    Acting Commissioner of Patents and Trademarks